US008623183B2

(12) United States Patent
Takenaka et al.

(10) Patent No.: US 8,623,183 B2
(45) Date of Patent: Jan. 7, 2014

(54) ELECTRODE MODULE

(75) Inventors: Shigeori Takenaka, Fukuoka (JP); Yoshiaki Hano, Fukuoka (JP); Minoru Yamada, Fukuoka (JP); Kimio Morimoto, Fukuoka (JP); Hiroshi Endo, Fukuoka (JP); Hiroshi Yasutake, Fukuoka (JP); Shinobu Sato, Fukuoka (JP); Keiichi Otsuka, Fukuoka (JP)

(73) Assignee: Kyushu Institute of Technology, Fukuoka (JP)

( * ) Notice: Subject to any disclaimer, the term of this patent is extended or adjusted under 35 U.S.C. 154(b) by 141 days.

(21) Appl. No.: 12/988,285

(22) PCT Filed: Apr. 2, 2009

(86) PCT No.: PCT/JP2009/056862
§ 371 (c)(1),
(2), (4) Date: Jan. 4, 2011

(87) PCT Pub. No.: WO2009/128346
PCT Pub. Date: Oct. 22, 2009

(65) Prior Publication Data
US 2011/0100812 A1 May 5, 2011

(30) Foreign Application Priority Data

Apr. 18, 2008 (JP) ................................. 2008-108731

(51) Int. Cl.
*G01N 27/403* (2006.01)
*G01N 27/28* (2006.01)

(52) U.S. Cl.
USPC ....................................... 204/286.1; 204/400

(58) Field of Classification Search
USPC .......................................................... 204/412
See application file for complete search history.

(56) References Cited

U.S. PATENT DOCUMENTS

| | | | |
|---|---|---|---|
| 5,466,575 A * | 11/1995 | Cozzette et al. | 435/6.11 |
| 6,153,070 A * | 11/2000 | Maurer et al. | 204/416 |
| 7,390,390 B2 * | 6/2008 | Yamamoto et al. | 204/604 |
| 2005/0137118 A1 * | 6/2005 | Silveri | 510/514 |
| 2005/0196776 A1 * | 9/2005 | Yang | 435/6 |
| 2005/0279634 A1 | 12/2005 | Ozaki et al. | |
| 2006/0008818 A1 * | 1/2006 | Chem et al. | 435/6 |
| 2006/0124458 A1 * | 6/2006 | Nauber et al. | 204/424 |

FOREIGN PATENT DOCUMENTS

| | | | |
|---|---|---|---|
| JP | 05-079989 A | 3/1993 |
| JP | 05-095223 A | 4/1993 |
| JP | 09-040372 A | 2/1997 |
| JP | 09-288080 A | 11/1997 |

(Continued)

*Primary Examiner* — Luan Van
*Assistant Examiner* — Steven Rosenwald
(74) *Attorney, Agent, or Firm* — Sughrue Mion, PLLC (57) ABSTRACT

An electrode module includes a working electrode, a counter electrode, a reference electrode and a well (container) for retaining an electrolytic solution and is used in electrochemical measuring instruments. This electrode module is produced by integrating the well with at least one of the working electrode, the counter electrode and the reference electrode. This integrated electrode includes a chip-like electrode having a thin membrane of an electrode material formed on the surface of a chip-like base metal. This chip-like electrode is disposed on and integrated with the bottom of the well in a detachable manner. There is provided the compact, low price electrode module of high repetition use efficiency with no need of maintenance and having easy handling.

4 Claims, 6 Drawing Sheets

(56) References Cited

FOREIGN PATENT DOCUMENTS

| | | | |
|---|---|---|---|
| JP | 11-014584 | A | 1/1999 |
| JP | 2005-530179 | A | 10/2005 |
| JP | 2005-345243 | A | 12/2005 |
| JP | 2007-514175 | A | 5/2007 |
| WO | 2005/001018 | A1 | 1/2005 |

* cited by examiner

FIG. 1

PRIOR ART

ELECTRODE MODULE

TECHNICAL FIELD

The present invention relates to a compact, low-cost electrode module used for electrochemical measuring instruments.

BACKGROUND ART

Recently, needs for techniques of carrying out diagnosis or analysis inexpensively in a short time are greatly increasing in the fields of bedside diagnosis carrying out medical diagnosis near a patient, various DNA diagnoses, etc. Of these, an electrochemical measuring method is an extremely simple, inexpensive measuring method that can detect a measuring object if there are simply present electrodes serving to measurement, and a system for applying voltage and current. In addition, a method of electrochemically detecting and measuring a specified substance in a liquid specimen by a method of using a working electrode, a counter electrode and a reference electrode is well-known (e.g., see Patent Documents 1 and 2), and also it is widely known that this method is applied to detection and measurement of DNA (e.g., see Patent Documents 3 and 4).

Figure 1:
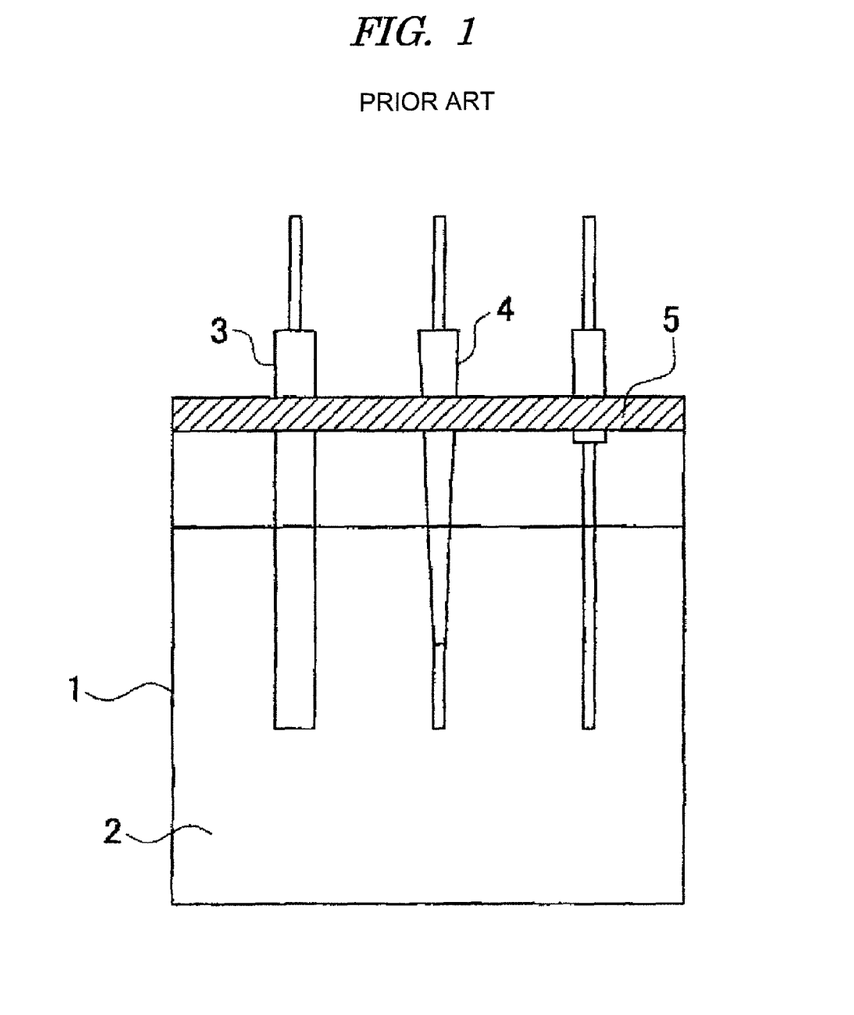
FIG. 1 is an entire block diagram of an electrode used for general electrochemical measurement.

In conventional electrodes used in electrochemical measurement, a general construction uses a rod-shaped electrode, for example, a gold electrode as a working electrode, for example, a silver-silver chloride electrode as a reference electrode, and for example, rod-shaped platinum as a counter electrode. FIG. 1 is an explanatory view for indicating the entire construction for a conventional electrochemical measurement method. Reference numeral 1 refers to a beaker (container for retaining an electrolytic solution), reference numeral 2 refers to an electrolytic solution, reference numeral 3 refers to a working electrode (e.g., a gold electrode), reference numeral 4 refers to a reference electrode (e.g., a silver-silver chloride electrode), and reference numeral 5 refers to a counter electrode (e.g., a platinum electrode). A commercially available beaker is used as the container for retaining the electrolytic solution, and as shown in FIG. 1, the various electrodes are maintained from above and placed in the electrolytic solution for electrochemical measurement.

The structure of the rod-shaped gold electrode as the working electrode uses for the tip end a material produced by molding, for example, rod-shaped gold with PEEK (polyether ether ketone) resin. This electrode can be repeatedly used by cleaning. Moreover, when the golf surface is deteriorated with flaws or the like, or in an experiment needed for uniformity of the gold surface such as immobilization of DNA, diamond for polishing and an alumina abrasive are used to polish the surface like a mirror finished surface on a glass plate for use.

In addition, in the case where the frequency in use is limited and there is relatively much time, for example, the electrode is experimentally used in a laboratory or the like, even such construction is sufficient in practical use. However, even in the use in such laboratory, when the frequency in use is high and there is little time in laboratory work, posing the problem of poor maintenance such as polishing. Moreover, considering the case where a measuring instrument using such electrode is used in the market as a product, there is a large obstacle for commercialization also from the viewpoints of cost performance, operability and maintenance.

Figure 2:
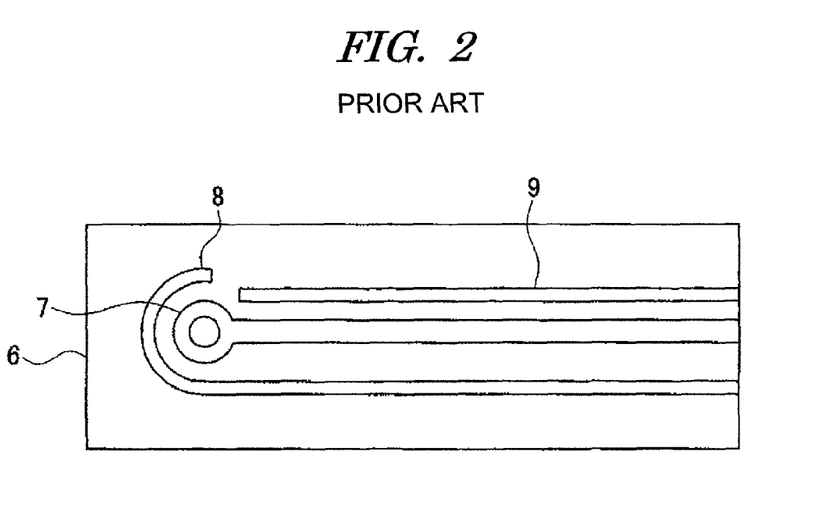
FIG. 2 is a block diagram of a glass electrode chip.

A printed electrode is known that involves formation of three electrodes, i.e., a working electrode 7, counter electrode 8, and reference electrode 9 on the surface of a glass substrate 6 by a printing technique, for example, as shown in FIG. 2, as improvement measures for the above problems. However, such electrode is problematic in that the price is very expensive, the repeated reuse is limited, and the like. Moreover, an electrode configured to integrate analysis electrodes and an address electrode in a container (cuvette) for an electrolytic solution is proposed in Patent Document 5. However, this electrode also has a complex construction and might be extremely high in cost. In addition, although a complex sensor array for analyzing small amounts of multicomponents made by microfabrication and the like are proposed (Patent Document 6), the problems of electrode modules as described above are not solved yet.

Patent Document 1: Japanese Patent Laid-Open Publication No. 05-79989

Patent Document 2: Japanese Patent Laid-Open Publication No. 05-95223

Patent Document 3: Japanese Patent Laid-Open Publication No. 09-40372

Patent Document 4: Japanese Patent Laid-Open Publication No. 09-288080

Patent Document 5: Japanese Patent Laid-Open Publication No. 11-14584

Patent Document 6: Japanese Unexamined Patent Application Publication No. 2005-530179

DISCLOSURE OF THE INVENTION

Problems to be Solved by the Invention

Thus, the subject to be solved in the present invention is to provide a simple and easy, inexpensive apparatus by solving all the problems of poor maintenance of an electrode section including a working electrode, high cost, poor handleability due to a large shape, poor efficiency in repeated reuse, etc. presently included in devices such as electrodes used in electrochemical measurement.

Means for Solving the Problems

The subject of the above present invention is achieved by the present invention as described in the following embodiments.

The invention described in embodiment 1 is an electrode module including a working electrode, a counter electrode, a reference electrode and a well (container) for retaining an electrolytic solution, used in an electrochemical measuring instrument, wherein the electrode module is produced by integrating the above well with at least one of the above working electrode, counter electrode and reference electrode, wherein the integrated electrode includes a chip-like electrode (electrode chip) having a thin membrane of an electrode material formed on the surface of a chip-like base metal, and wherein the chip-like electrode is disposed on and integrated with the bottom of the above well in a detachable manner.

The electrode module in the invention stands for a collectively replaceable part or component including at least an electrode and a well (container) in an electrochemical measuring apparatus. As is apparent from the description below, the electrode module in the invention includes, in addition to the electrode and the well, a material produced by combining or incorporating an electrode presser for fixing an electrode tip, an electrode holding ruler, an electrode holder or the like, for holding electrodes or the like. Additionally, chip-like in the invention means thin piece-like. Moreover, the integration of an electrode with a well stands for a state in which the electrode is integrally and structurally freely detachably combined with the well.

The invention described in embodiment 2 is the electrode module described in embodiment 1, wherein the chip-like electrode is formed on the surface of a chip-like base metal in thin film shape using an electrode material by any one method of depositing, sputtering and printing.

The invention described in embodiment 3 is the electrode module described in embodiment 1 or 2, wherein the working electrode and/or the counter electrode is integrated with the well.

The invention described in embodiment 4 is the electrode module described in embodiment 1 or 2, wherein the working electrode, the counter electrode and the reference electrode are all integrated with the well.

The invention described in embodiment 5 is an electrode chip including a thin membrane of an electrode material formed on the surface of a chip-like base metal, for the electrode module described in embodiment 1.

In addition, there is provided an electrochemical measuring instrument using the electrode module described in embodiment 1.

Advantages of the Invention

In the electrode module of the invention, for example, as the working electrode is used a chip-like material made by forming a metal to be an electrode on the surface of a metal to be a base in thin film shape. This chip-like electrode is used to integrate with a well for use. This electrode chip is detached from the well and is formed into a structure so as to be replaceable readily in itself. In addition, in this working electrode, for example, the deposited metal surface can be greatly smoothed by polishing the surface of the metal to be the base, so that the electrode has the advantage of being able to be also used, for example, in an experiment in which DNA is immobilized to the gold surface to identify an enzyme or the like. Additionally, the thickness of gold to be deposited is very thin, and therefore the amount of gold used for the electrode is very small, whereby the electrode has the advantage of be able to be fabricated at a low cost.

In the present invention, the electrode chip is integrated with the well and only the electrode chip is configured to be easily replaceable, so that a container such as a beaker is also not needed to be used and thus the electrode section is very compact, offering the advantage of being capable of improvement in operability. Although the electrode chip of the invention is reusable by cleaning the electrode module, when the electrode chip surface is damaged, only the electrode chip made relatively inexpensively may be changed. Moreover, the electrode chip of the invention has a simple structure and is also recyclable after recovery. This makes it possible to provide an electrode module that does not need maintenance such as polishing and is repeatedly reusable.

BEST MODE FOR CARRYING OUT THE INVENTION

An electrochemical measuring apparatus in the invention includes a well for retaining a working electrode, a counter electrode, a reference electrode and an electrolytic solution, and is used to measure the electrochemical response of a specific substance included in the electrolytic solution. Various amperometry and voltammetry modes are suitable although the method of measuring the electrochemical response is not particularly limited.

Amperometry is an approach that measures and analyzes the current flowing through electrodes to the potential step against time and is widely used in quantitative analysis on electrochemically active species in an electrolytic solution. Voltammetry is widely used as an approach that measures the response current when the electrode potential is changed. The examples of voltammetry include cyclic voltammetry that changes the electrode potential linearly and pulse voltammetry that changes the electrode potential by pulse. The resulting response current value depends on the concentration of an electrochemically active species in an electrolytic solution. The electrochemical measuring apparatus in the invention measures the electrochemical responses of various activated substrates generated in an electrolytic solution by using such well-known electrochemical process and means, and carries out qualitative or quantitative analysis of a specific substance.

The electrode module of the invention used in the above electrochemical measuring instrument is made by integrating the above well with at least one of the above working electrode, counter electrode and reference electrode, the integrated electrode includes a chip-like electrode (electrode chip) having an electrode material thin membrane formed on the surface of a chip-like base metal, and the chip-like electrode is disposed on and integrated with the bottom of the above well in a detachable manner (freely detachable). Hereinafter, the electrode module of the invention will be described with reference to drawings.

Figure 3:
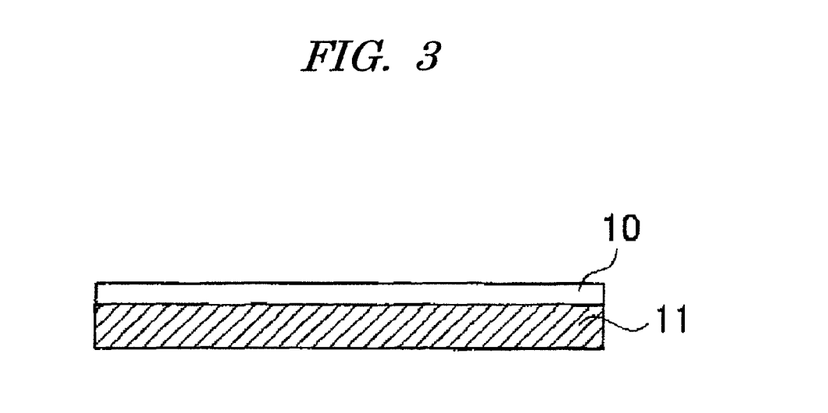
FIG. 3 is a block diagram of an electrode chip in the invention.

FIG. 3 is an explanatory view that shows one example of the structure of the electrode chip used in the invention. Reference numeral 11 is a chip-like base metal such as titanium, and reference numeral 10 is a thin membrane of an electrode material such as gold formed on its surface, for example, by deposition. The method of forming a thin membrane of an electrode material is not particularly limited; however, the membrane is preferably formed in thin film shape by any method of depositing, sputtering or printing. Well-known methods of physical vapor deposition (PVD) and chemical vapor deposition (CVD), etc. can be utilized as deposition. Moreover, the thin membrane may be formed by a sputtering technique, a kind of physical vapor deposition. Alternatively, the thin membrane can also be formed using a well-known printing technique.

The electrode module of the invention is a collectively replaceable part or a component, including an electrode, in an electrochemical measuring apparatus, and more specifically a part or a component integrally combined with a well on the bottom of which is disposed in a detachable manner at least one of a working electrode, counter electrode and reference electrode comprising the above electrode chip.

Figure 4:
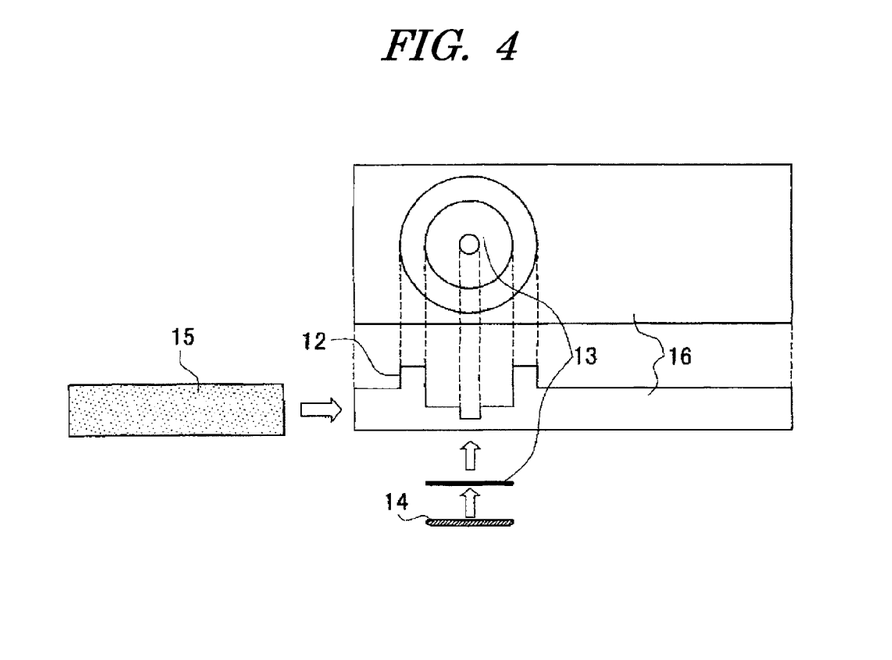
FIG. 4 is a diagram for depicting the structure of one example of the electrode module of the invention.
Figure 5:
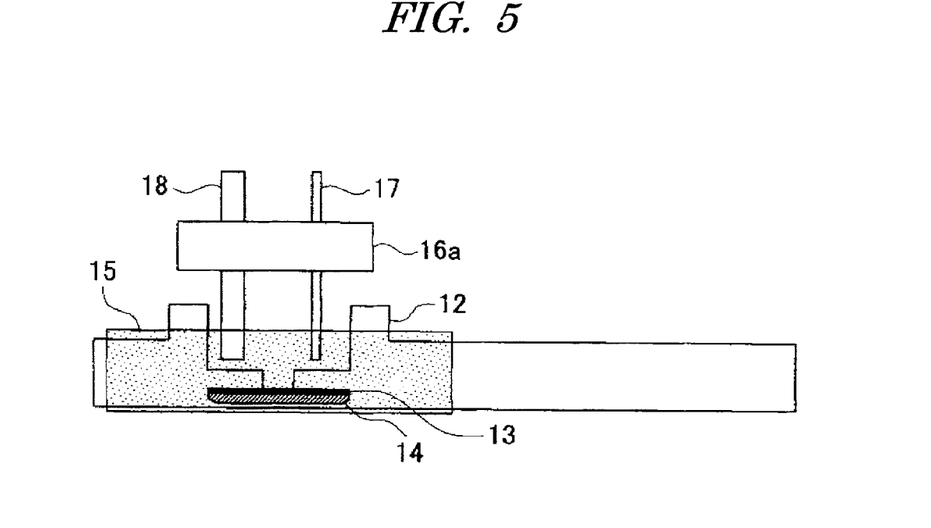
FIG. 5 is a block diagram of an electrochemical measuring apparatus that uses the electrode module of the invention.

FIGS. 4 and 5 illustrate an example making up of the electrode module of the invention in which the working electrode (as in the case of the counter electrode) is integrated with the well. FIGS. 4 and 5 are schematic diagrams depicting the construction of the electrode module. In FIG. 4, reference numeral 12 indicates a well (container), reference numeral 13 indicates a working electrode (working electrode chip), reference numeral 14 indicates an electrode presser, reference numeral 15 indicates an electrode holding ruler, and reference numeral 16 indicates an electrode holder. Although the electrode holding ruler 15 is used to immobilize the working electrode chip 13 to the well, if the electrode presser 14 made from an elastic, electrically conductive resin rubber (doom-like) is used medially, the working electrode chip 13 can be uniformly pressed and fixed to the well 12, as shown in FIG. 5.

Moreover, the working electrode chip 13 is slidable on the well with one touch and thus simply installable and detachable. In FIG. 5, reference numeral 16a indicates an electrode holder (measuring instrument side), reference numeral 17 indicates a counter electrode (measuring instrument side) and reference numeral 18 indicates a reference electrode (measuring instrument side).

Figure 6:
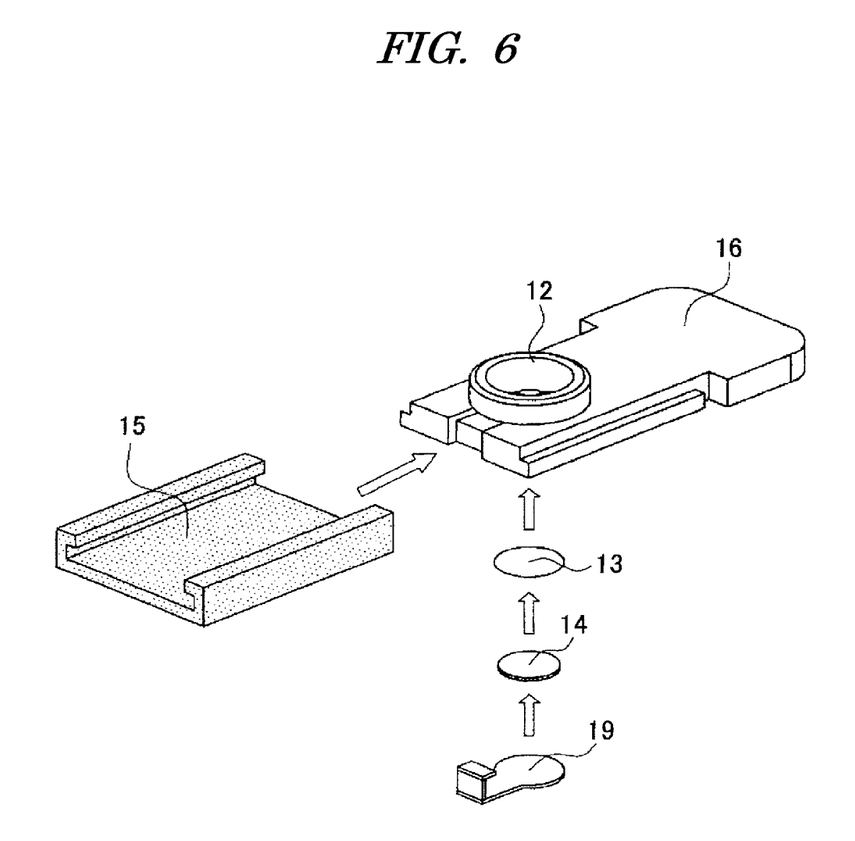
FIG. 6 is a diagram illustrating one example of how to assemble the electrode module of the invention.

FIG. 6 is a diagram illustrating one example of how to assemble the electrode module schematically shown in FIGS. 4 and 5 above. The electrode holding ruler 15 has a shape that holds the underside of the working electrode 13 and electrode presser 14 till the well 12 and is slid to the electrode holder 16 for installation. In this case, an electrode conductive plate 19 for electrode conduction can also be inserted into the underside of the electrode presser 14.

The electrode module of the invention is preferably a module in which a working electrode or counter electrode is integrated with a well as illustrated in FIGS. 4 and 5. In addition, as not shown in a drawing particularly, an electrode module in which a working electrode and a counter electrode are both integrated with a well is also preferred.

Figure 7:
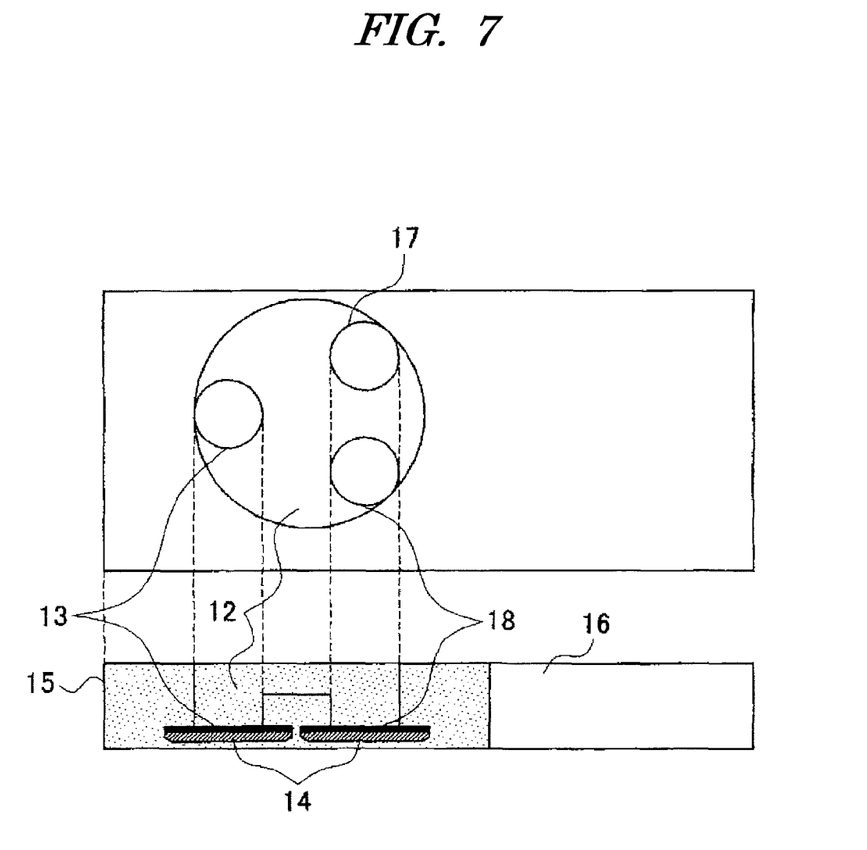
FIG. 7 is a block diagram of the electrode module that coplanarly distributes a working electrode, a counter electrode and a reference electrode of the invention.

Another preferred embodiment of the invention is an electrode module in which a working electrode, a counter electrode and a reference electrode are all integrated with a well as shown in FIG. 7. FIG. 7 schematically shows a plan view and a sectional view of such electrode module, and reference numeral 13 indicates a working electrode (electrode chip), reference numeral 17 indicates a counter electrode, reference numeral 18 indicates a reference electrode, reference numeral 12 indicates a well, reference numeral 14 indicates an electrode presser, reference numeral 15 indicates an electrode holding ruler, and reference numeral 16 indicates an electrode holder.

Example 1

Hereafter, examples are shown in which the telomerase enzyme that works actively in most cancer cells is detected using the electrode module of the invention.

Cancer cells infinitely grow without extinction since telomerase enzymes repair the telomere. For example, a primer of being a part of a DNA structure is fixed onto the gold electrode surface and then a telomerase enzyme is reacted therewith to elongate the DNA. When a molecule having electrochemical activity called FND is reacted with therewith and a voltage is applied to the working electrode, the current value is changed depending on the length of the DNA. Determination of the change of the current value makes it possible to detect the presence or absence of telomerase enzymes, i.e., cancer cells.

An electrode module of the invention in which a working electrode is integrated with a well was set to an electrochemical measurement device as shown in FIG. 5. Reference numeral 16a indicates an electrode holder of the device and reference numerals 17 and 18 indicate a counter electrode and a reference electrode, respectively, which are set to the holder. The amount of an electrolytic solution that should be retained to a well 12 is sufficiently an extremely small amount (about 300 μL). A working electrode chip 13 was used in which one side of titanium foil polished to a mirror finished surface (membrane thickness: 50 μm, weight: about 11 mg) was degreased and then gold (99.99% or more pure) was formed thereon at a thin membrane thickness of about 700 to 800 angstroms (weight: about 0.08 mg) by sputtering. An electrode presser 14 is a doom-like, elastic, electrically conductive resin rubber and plays the role of uniformly suppressing the working electrode chip 13 for restraining liquid leakage. An electrode holding ruler 15 and the well 12 are made of polypropylene resin and inexpensive and exhibit durability both chemically and physically.

Figure 8:
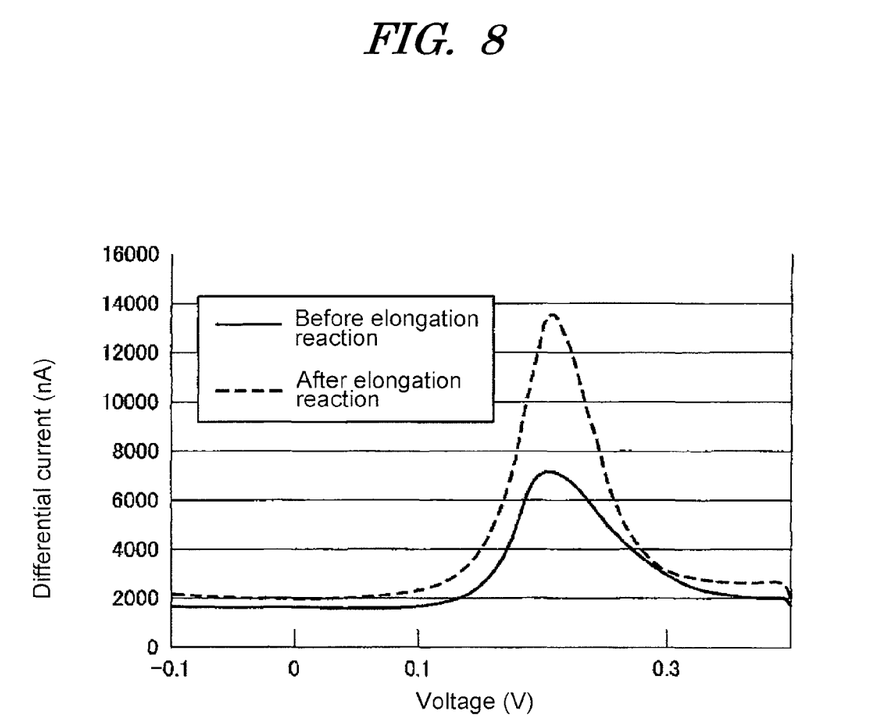
FIG. 8 is a DPV waveform diagram measured before and after DNA elongation reaction.

A primer of being a part of a DNA structure is fixed onto the gold electrode surface and then a telomerase enzyme is reacted therewith, causing the elongation of the DNA. When a molecule having electrochemical activity called FND is reacted with therewith and a voltage is applied to the working electrode, the current value is changed depending on the length of the DNA. Hence, determination of the change of the current value makes it possible to detect the presence or absence of telomerase enzymes. FIG. 8 shows DPV measurement waveforms before and after the DNA elongation.

Example 2

An electrode module of another aspect of the electrode chip of the invention was fabricated. The electrode module is fabricated by integrating all the working electrode, the counter electrode and the reference electrode with the well, as shown in FIG. 7. FIG. 7 schematically shows a plan view and a sectional view of such electrode module, and reference numeral 7 indicates the working electrode (electrode chip), reference numeral 8 indicates the counter electrode, reference numeral 9 indicates a reference electrode, reference numeral 12 indicates the well, reference numeral 14 indicates an electrode presser, reference numeral 15 indicates the electrode holding ruler, and reference numeral 16 indicates an electrode holder. The working electrode and the counter electrode used, respectively, electrodes made by forming thin membranes of gold and platinum on the surfaces of titanium, and the reference electrode used an electrode chip having a thin membrane of silver and silver chloride formed on the surface of titanium to thereby form a module. This made it possible to further miniaturize the device.

Industrial Applicability

Use of the electrode module of the invention makes it possible to achieve miniaturization of an electrochemical measuring apparatus that has been difficult so far and to materialize it as various chemical substance analyzers of a handy type.

The invention claimed is:
1. An electrode module for use in an electrochemical measuring instrument comprising:
an electrode chip comprising a chip-like metal base on which is a thin film of electrode material formed by any one of depositing, sputtering, and printing; and a well for retaining an electrolytic solution and having a bottom, the well being positioned in an electrode holder, wherein the electrode chip is disposed on and integrated with the bottom of the well in a detachable manner so as to form at least part of an internal surface of the well, wherein an electrode holding ruler is used to fix the electrode chip to the well, the electrode holding ruler having a planar base and parallel slits along two opposing side walls of the base, wherein the electrode module further comprises an electrode presser and a conductive plate, the electrode presser being made from an elastic, electrically conductive resin rubber, and the conductive plate having a clamping portion which engages a groove in the electrode holder, wherein the conductive plate is positioned on the electrode holding ruler, the electrode presser is positioned on the conductive plate, and the electrode chip is positioned on the electrode presser.

2. The electrode module of claim 1 wherein the electrode chip is a working electrode chip.

3. The electrode module of claim 1 wherein the electrode chip is a counter electrode chip.

4. The electrode module of claim 1 wherein the electrode chip is a reference electrode chip.

* * * * *